United States Patent
Bergersen (10) Patent No.: US 9,517,113 B2
(45) Date of Patent: Dec. 13, 2016

(54) ORAL APPLIANCE, SYSTEM AND METHOD FOR CORRECTING CLASS III PROBLEMS OF MANDIBULAR PROGNATHISM

(71) Applicant: Ortho-Tain, Inc., Winnetka (IL)

(72) Inventor: Earl O. Bergersen, Dorado, PR (US)

(73) Assignee: Ortho-Tain, Inc., Winnetka, IL (US)

( * ) Notice: Subject to any disclaimer, the term of this patent is extended or adjusted under 35 U.S.C. 154(b) by 70 days.

(21) Appl. No.: 14/029,175

(22) Filed: Sep. 17, 2013

(65) Prior Publication Data
US 2015/0079530 A1    Mar. 19, 2015

(51) Int. Cl.
*A61C 3/00*     (2006.01)
*A61C 7/36*     (2006.01)
*A61C 7/08*     (2006.01)

(52) U.S. Cl.
CPC .. *A61C 7/36* (2013.01); *A61C 7/08* (2013.01)

(58) Field of Classification Search
CPC ............... A61C 7/36; A61C 7/08; A61F 5/56
USPC .................................. 433/6, 80; 128/861–862
See application file for complete search history.

(56) References Cited

U.S. PATENT DOCUMENTS

| | | | |
|---|---|---|---|
| 3,478,742 A * | 11/1969 | Bohlmann ................ 433/6 |
| 4,139,944 A | 2/1979 | Bergersen |
| 5,592,951 A * | 1/1997 | Castagnaro ............. A61F 5/566 |
| | | | 128/848 |
| 5,624,257 A | 4/1997 | Farrell |
| 5,645,420 A | 7/1997 | Bergersen |
| 5,682,903 A * | 11/1997 | Meade ......................... 128/848 |
| 5,876,199 A | 3/1999 | Bergersen |
| 7,234,933 B2 | 6/2007 | Bergersen |
| 7,458,810 B2 | 12/2008 | Bergersen |
| 7,716,062 B2 | 5/2010 | Bergersen |
| 7,963,765 B2 | 6/2011 | Bergersen |
| 7,975,701 B2 | 7/2011 | Bergersen |
| 2003/0224312 A1 | 12/2003 | Bergersen |
| 2003/0224313 A1* | 12/2003 | Bergersen ................. 433/6 |
| 2004/0058295 A1* | 3/2004 | Bergersen ................. 433/6 |
| 2004/0152032 A1 | 8/2004 | Bergersen |
| 2006/0084024 A1 | 4/2006 | Farrell |
| 2007/0240724 A1* | 10/2007 | Bergersen ............. 128/861 |
| 2012/0196243 A1* | 8/2012 | Farrell ..................... 433/6 |
| 2013/0244194 A1 | 9/2013 | Bergersen |

FOREIGN PATENT DOCUMENTS

FR       2867058 A1    9/2005

* cited by examiner

*Primary Examiner* — Heidi M Eide
(74) *Attorney, Agent, or Firm* — Taft Stettinius & Hollister, LLP; Ryan O. White (57) ABSTRACT

An oral appliance, a system and a method for correcting malocclusions may cause teeth and/or jaws of the patient to move into a corrected position. An upper body and a lower body of the appliance may be connected by a hinge. Lingual protrusions may extend rearward from the anterior portion of the upper body and contact the maxilla of the patient when the appliance is worn. A protrusion may extend from the anterior portion of the lower body forward relative to the mouth and contact the lips and exert a rearward force against the lower teeth.

16 Claims, 8 Drawing Sheets

ORAL APPLIANCE, SYSTEM AND METHOD FOR CORRECTING CLASS III PROBLEMS OF MANDIBULAR PROGNATHISM

BACKGROUND OF THE INVENTION

The present invention relates to an oral appliance, a system and a method for correcting a malocclusion. More specifically, the present invention relates to an oral appliance, a system and a method, in conjunction with wearing of the oral appliance, to correct a malocclusion, in particular, mandibular prognathism.

It is generally known to provide dental care to a patient. Typically, the patient may visit, for example, a dentist, an orthodontist or other type of care provider at the office of the care provider. The dentist, for example, may examine the patient using various techniques, including imaging and/or x-raying the oral area and/or jaws. After reaching a diagnosis, the dentist may then provide the patient with an oral appliance to correct the condition of the patient.

In addition to the oral appliance, the dentist may provide the patient with instructions for exercises to perform while wearing the oral appliance. The exercises may cause, for example, the teeth to move toward a corrected position and may assist in correcting the malocclusion. In the case of mandibular prognathism, the oral appliance and the exercises may advance the maxilla, retract the mandible and produce an overjet and overbite which may be ideal to correct and/or prevent a future Class III problem, such as lower jaw excess in the patient.

However, the exercises may be tedious and/or time-consuming for the patient. In some cases, the exercises may cause pain to the patient. Accordingly, the patient may not be motivated to perform the exercises and may abandon them or otherwise not regularly perform the exercises to assist with and/or to correct the malocclusion. As a result, the malocclusion may not be corrected to completion. In other cases, the patient may not have time to perform the exercises. Failure to perform the exercises may prevent or otherwise hinder complete correction of a malocclusion.

For example, one particular condition is prognathism. Prognathism may be the positional relationship of the mandible and/or maxilla to the skeletal body where either of the jaws protrudes beyond a predetermined imaginary line in the coronal plane of the skull. The maxillae may consist of paired maxillary bones or maxilla; or two halves that may be fused at the intermaxillary suture to form the upper jaw. Similarly, the lower jaw or mandible may be a fusion of two halves at the mandibular symphysis. Prognathism may also be used to describe ways that the maxillary dental arches and/or the mandibular dental arches relate to one another, including a malocclusion in which the upper teeth and/or the lower teeth do not align.

In general dentistry, oral surgery, maxillofacial surgery and/or orthodontics, prognathism may be assessed clinically or radiographically using cephalometrics. One or more types of prognathism may result in the common condition of malocclusion including overbite, in which the top teeth and/or the lower teeth of the patient do not align properly. Cephalometric analysis may be the most accurate way of determining all types of prognathism, since such analysis may include assessments of skeletal body, occlusal plane angulation, facial height, soft tissue assessment and anterior dental angulation. Various calculations and assessments of the information in a cephalometric radiograph may allow the clinician to objectively determine dental relationships and/or skeletal relationships and determine a plan of correction.

In particular, mandibular prognathism is a Class III malocclusion with a dentofacial anomaly affecting the lower third of the face. Mandibular prognathism may be characterized by protrusion of the mandible with lower incisors often overlapping the upper incisors. The protruding lower jaw may be caused by a forward positioning of the mandible itself.

To obtain the best results in correcting Angle Class III malocclusions, the etiologies of the malocclusion may first be clarified, and then an appropriate modality may be decided. Angle Class III malocclusions may be classified into three categories. Type A is true mandibular prognathism, which means that the maxilla is normal but the mandible may be overgrown. Type B is characteristic of the overgrown maxilla and mandible with anterior crossbite. Type C indicates a hypoplastic maxilla with anterior crossbite. Modalities may be differentially decided according to the classification of Angle Class III malocclusions.

For many Class III malocclusions, surgery may be the best alternative. Depending on the amount of skeletal discrepancy, surgical correction may consist of mandibular setback, maxillary advancement or a combination of mandibular and maxillary procedures. After surgical correction of the skeletal discrepancy, the occlusion may usually be finished orthodontically to a Class I relationship.

The surgical correction of Class III malocclusion, in particular, mandibular prognathism, may be undertaken in a variety of ways, e.g. a bilateral sagittal split osteotomy to retract the mandible or a Le Fort I procedure to advance the maxilla, or a combination of these procedures. However, the associated surgical risks and complications must be considered, as well as the increased expense.

If a non-surgical alternative may be capable of producing results comparable with those that may be achieved surgically, then a dentist and/or orthodontist may consider and/or suggest such a non-surgical approach to the patient. In some cases, a non-surgical approach may be the preferred choice of the dentist, orthodontist and/or the patient.

For example, facial growth modification may be an effective method of resolving skeletal Class III jaw discrepancies in growing children. Dentofacial orthopedic appliances, including the chin cup, face mask, maxillary protraction combined with chin cup traction and the Frankel functional regulator III appliance may be used. Orthognathic surgery in conjunction with orthodontic care may be required for the correction of mandibular prognathism in an adult patient. Typically, many oral appliances have an upper labial shield and a lower labial shield to receive and/or move the dentition of the patient. In certain cases, either the upper dentition may be moved or the lower dentition may be moved. In other instances, the upper dentition and the lower dentition may be moved. If the upper labial shield may not be provided, then the upper arch and the whole upper dentition may be pushed forward by the appliance.

A need, therefore, exists for a non-surgical approach for correcting mandibular prognathism in a patient of a young age. A need also exists for an oral appliance and a method for reducing an amount of patient cooperation and/or exercises required for correcting a malocclusion, in conjunction with wearing of the oral appliance, to correct a malocclusion, in particular, mandibular prognathism.

SUMMARY OF THE INVENTION

The present invention relates to an oral appliance and a method for correcting a malocclusion. More specifically, the present invention relates to an oral appliance, a system and a method, in conjunction with wearing of the oral appliance, to correct a malocclusion, in particular, mandibular prognathism.

To this end, in an embodiment of the present invention, an appliance for correcting a malocclusion in a mouth of a user is provided. The user has lips, a tongue, a maxilla and teeth. The teeth have upper incisors and lower incisors. The appliance may have a generally U-shaped upper body with an anterior portion adjacent to the incisors and a posterior portion located rearward to the anterior portion. The upper body may have an upper base with a perimeter defining an outer boundary of the upper base. The upper body may have walls extending along the perimeter of the posterior portion of the upper body. The appliance may also have a generally U-shaped lower body with an anterior portion adjacent to the incisors. The lower body may have a lower base with a perimeter defining an outer boundary of the lower base. The lower base has a width which is greater than a width of the teeth of the user. The lower body may have walls extending along the perimeter of the lower body defining a trough in the lower body. Lingual protrusions may extend rearward from the anterior portion of the upper body. The lingual protrusions may contact the maxilla of the user when the appliance is worn within the mouth of the user. A protrusion may extend from the anterior portion of the lower body forward relative to the mouth. The protrusion may contact the lips of the user when the appliance is worn within the mouth of the user and may exert a rearward force against the lower teeth.

In an embodiment, the appliance may have a raised surface on the posterior portion of the upper base of the upper body.

In an embodiment, the appliance may have a shelf that projects generally horizontally from the upper body. The shelf may be adjacent to the upper anterior base, may extend rearward in the mouth of the user and may provide a surface that guides the tongue when the appliance is worn within the mouth of the user.

In an embodiment, the appliance may have a ramp that may extend at an angle relative to the upper base on the anterior portion of the upper body. The ramp may exert a force on the upper incisors and may guide the upper incisors forward and downward when the appliance is worn within the mouth of the user.

In an embodiment, the upper base may contact teeth furthest within the mouth.

In an embodiment, the appliance may have a raised protrusion on one of the lingual protrusions. The raised protrusion may direct the tongue when the appliance is worn within the mouth of the user.

In an embodiment, the appliance may have a reline material in contact with the trough in the lower body. The reline material may adhere the lower body to the lower teeth and may exert a force against the lower teeth when the appliance is worn in the mouth of the user.

In an embodiment, the appliance may be constructed from a resilient material.

In an embodiment, the trough may have a roughened surface.

In an embodiment, the lingual protrusions may have a center tab extending rearward from a center of the anterior portion of the upper body and a side tab adjacent to each side of the center tab extending rearward from the anterior portion of the upper body. The lingual protrusions may contact the maxilla of the user when the appliance is worn within the mouth of the user.

In an embodiment, the lower base may have a flat surface.

In another embodiment of the present invention, a method for correcting a malocclusion of a patient is provided. The patient has a mouth with upper teeth having upper incisors, lower teeth, a palate, a tongue and lips. The method may have the step of inserting an appliance into the mouth of the patient having the malocclusion. The appliance has an upper body and a lower body wherein the lower body is below the upper body. The upper body may have an anterior portion with an angled surface and a lingual tab extending rearward and a posterior portion having an elevated occlusal surface. The lower body may have a shield extending from the lower body. The shield may surround the lower teeth when the lower body is placed in the mouth. The lower body may have an anterior extension and a trough. The method may have the step of pressing the tongue against the upper body of the appliance so that the lingual tab of the upper body contacts the palate when the appliance is worn in the mouth of the patient. The method may also have the step of pushing the lower teeth in a rearward direction in the mouth of the patient so that the lips contact the anterior extension of the lower body.

In an embodiment, the method may have the step of depressing posterior upper teeth so that the elevated occlusal surface contacts the posterior upper teeth.

In an embodiment, the method may have the step of guiding the upper incisors forward and downward relative to the mouth of the patient so that the angled surface contacts the upper incisors.

In an embodiment, the method may have the step of adding a reline material to the trough of the lower body so that the reline material contacts the lower teeth.

In an embodiment, the method may have the step of surrounding the lower teeth with a curable material so that the curable material forms a lining conforming to the lower teeth when cured.

In a further embodiment of the present invention, an orthodontic system worn adjacent to upper teeth and lower teeth in a mouth of a user is provided. The user has an upper jaw, a lower jaw, lips and a tongue. The upper teeth have upper incisors and upper molars and the lower teeth have lower incisors and lower molars. The orthodontic system may have an upper appliance with an anterior portion and a posterior portion located rearward of the anterior portion. The posterior portion of the upper appliance may be shaped to contact the upper molars. The system may have a lower appliance with an outer shield extending vertically downward from the lower appliance defining a trough in the lower appliance. The lower appliance may be shaped to contact the lower incisors and the lower molars. The system may have a lining in contact with the lower teeth in the trough in the lower appliance. The lining may adhere the lower appliance to the lower teeth and may exert a force against the lower teeth when the appliance is worn in the mouth of the user. The system may have a tab extending rearward from the anterior portion of the upper appliance to contact the upper jaw of the user and move the upper jaw forward relative to the lower jaw when the appliance is worn within the mouth of the user. The system may also have a bumper that extends from the outer shield of the lower appliance forward relative to the mouth of the user so that the lips exert a rearward force against the bumper and move the lower jaw rearward relative to the upper jaw when the lower appliance is worn within the mouth of the user.

In an embodiment, the system may have a shelf in the upper appliance. The shelf may form a cavity with the tab behind the anterior portion of the upper appliance.

In an embodiment, the system may have a hinge that connects the upper appliance to the lower appliance.

In an embodiment, the system may have an elevated surface on the posterior portion of the upper appliance. The elevated surface may be shaped to depress the upper molars when the upper appliance is worn within the mouth of the user.

In yet another embodiment of the invention, an appliance for correcting a malocclusion in a mouth of a user is provided. The appliance may have a generally U-shaped upper body having an anterior portion adjacent to the upper incisors and a posterior portion located rearward to the anterior portion. The upper body may have an outer perimeter and an inner perimeter located interior to the outer perimeter. The upper body may have an upper labial shield extending along the outer perimeter of the upper body. A generally U-shaped lower body having an outer perimeter may have a lower labial shield extending along the outer perimeter of the lower body. Lingual protrusions may extend generally upward from the posterior portion of the inner perimeter of the upper body. The lingual protrusions may contact the palate of the user when the appliance may be worn within the mouth of the user.

It is, therefore, an advantage of the present invention to provide an oral appliance and a method for correcting a malocclusion using the oral appliance.

Another advantage of the present invention is to provide an oral appliance and a method for correcting a malocclusion using the oral appliance which may reduce an amount of time required for correcting the malocclusion.

Yet another advantage of the present invention is to provide an oral appliance and a method for correcting a malocclusion using the oral appliance which may reduce an amount of exercise required by the patient to correct the malocclusion.

Another advantage of the present invention is to provide an oral appliance and a method for correcting a malocclusion using the oral appliance wherein a patient may wear the oral appliance during a period of nighttime passive wear.

An advantage of the present invention is to provide an oral appliance and a method for correcting a malocclusion wherein a greater percentage of patients may be motivated to wear the oral appliance to correct the malocclusion.

Still another advantage of the present invention is to provide an oral appliance and a method for correcting a malocclusion which may adhere to the teeth of the patient with passive wear of the oral appliance during, for example, sleeping.

A further advantage of the present invention is to provide an oral appliance and a method for correcting a malocclusion wherein the oral appliance may place pressure on the front and/or rear teeth.

Moreover, an advantage of the present invention is to provide an oral appliance and a method for correcting a malocclusion wherein the oral appliance may be worn on a lower arch and an upper arch simultaneously.

A further advantage of the present invention is to provide an oral appliance and a method for correcting a malocclusion without requiring a biting force to be applied by a user.

Another advantage of the present invention is to provide an oral appliance and a method for correcting a malocclusion wherein the oral appliance has one or more shields which are shaped to prevent movement of the oral appliance away from teeth and may provide movement of teeth into a correct position.

Moreover, an advantage of the present invention is to provide an oral appliance and a method for correcting a malocclusion wherein the oral appliance may contact the palate to provide pressure against the palate to widen the palate and/or advance the palate in a forward direction.

Another advantage of the present invention is to provide an oral appliance and a method for correcting a malocclusion wherein the oral appliance has a retentive ability which may prevent the oral appliance from slipping from the teeth and may move the teeth efficiently.

A further advantage of the present invention is to provide an oral appliance and a method for correcting a malocclusion wherein the oral appliance may have an interior surface for more than one tooth.

Another advantage of the present invention is to provide an oral appliance and a method for correcting malocclusions which enables alignment of an upper jaw and a lower jaw.

Yet another advantage of the present invention is to provide an oral appliance and a method for correcting malocclusions which may have an appliance made of a resilient material.

Still further, an advantage of the present invention is to provide an oral appliance and a method for correcting malocclusions which may have tabs on the upper lingual area to encourage the tongue to assume an elevated position to encourage a widening of the upper arch of the palate.

Also, an advantage of the present invention is to provide an oral appliance and a method for correcting malocclusions which may have palatal tabs on the posterior portion of the upper body to encourage the tongue to exert pressure against the palatal tabs to encourage a widening of the palate.

Another advantage of the present invention is to provide an oral appliance and a method for correcting malocclusions which may have a protrusion in the upper lingual area at the midline to remind the tongue to thrust forward during use.

A further advantage of the present invention is to provide an oral appliance and a method for correcting malocclusions which may have an elevation in the upper lingual area of the appliance to remind the patient where to place the tongue during use.

Another advantage of the present invention is to provide an oral appliance and a method for correcting malocclusions which may have a reminder bump in the upper lingual area of the appliance to remind the patient where to place the tongue during use.

Yet another advantage of the present invention is to provide an oral appliance and a method for correcting malocclusions which may move the lower jaw back to correct Class III type jaw relations, such as lower jaw protrusions.

Still further, an advantage of the present invention is to provide an oral appliance and a method for correcting malocclusions which may have almost complete elimination of the anterior lingual shield in combination with an elevated posterior area of the appliance to allow the posterior teeth to be pushed in an upper direction by the tongue pressing on the teeth from the lingual.

An advantage of the present invention is to provide an oral appliance and a method for correcting malocclusions which may provide appliances in various arch shapes, such as square, tapered or normally shaped arches.

Yet another advantage of the present invention is to provide a oral appliance and a method for correcting malocclusions which may utilize material, such as rubber, silicone, acrylic, or the like on the appliance in any area to increase the retainability or fit of the appliance as well as to stop movement of teeth in this area.

Moreover, an advantage of the present invention is to provide a oral appliance and a method for correcting malocclusions which may provide appliances of various sizes to correct malocclusions and straighten the teeth at various ages in the deciduous, mixed and/or adult dentitions and either prevent problems from developing and/or correcting the same problems.

Still further, an advantage of the present invention is to provide an oral appliance and a method for correcting malocclusions which may control the eruption of teeth and/or depress certain teeth to correct the malocclusion.

Yet another advantage of the present invention is to provide an oral appliance and a method for correcting malocclusions which may straighten the teeth sufficiently to avoid regular braces and/or other types of orthodontics at a later stage.

An advantage of the present invention is to provide a oral appliance having and a method for correcting malocclusions which may correct jaw relations whether the case is in an Angle Class I with normal jaw and/or molar relation, Class II having low jaw and/or molars back from a normal position or Class III having a low jaw and/or molars forward in position.

Also, an advantage of the present invention is to provide an oral appliance and a method for correcting malocclusions wherein the appliance may be manufactured with various resiliency and/or stiffness to be more comfortable and/or more efficient in correcting certain problems.

Still another advantage of the present invention is to provide an oral appliance which may prevent choking and/or swallowing of the oral appliance.

A further advantage of the present invention is to provide an oral appliance and a method for correcting an occlusal bite of a patient.

Yet another advantage of the present invention is to provide an oral appliance and a method for correcting a malocclusion of a young person.

An advantage of the present invention is to provide an oral appliance and a method for correcting a malocclusion of a person while permanent and/or deciduous teeth are present and/or erupting in the mouth.

A further advantage of the present invention is to provide an oral appliance and a method for correcting a malocclusion of a person by guiding the erupting teeth into a desired position in the mouth.

Yet another advantage of the present invention is to provide an oral appliance and a method which corrects a malocclusion in a short amount of time.

Still further, an advantage of the present invention is to provide a method for correcting a malocclusion of a patient which requires only one oral appliance.

Yet another advantage of the present invention is to provide an oral appliance and a method for correcting a malocclusion of a patient that is inexpensive.

Still another advantage of the present invention is to provide an oral appliance and a method for correcting a malocclusion of a patient which is appealing to the public.

Further, an advantage of the present invention is to provide an oral appliance and a method for correcting a malocclusion of a patient which requires few, if any, adjustments and/or few, if any, appointments by a dentist or orthodontist.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to an oral appliance and a method for correcting a malocclusion. More specifically, the present invention relates to an oral appliance, a system and a method, in conjunction with wearing of the oral appliance, to correct a malocclusion, in particular, mandibular prognathism.

Referring now to the drawings, wherein like numerals refer to like parts, FIGS. 1-6 illustrate various views of an embodiment of an appliance 10 for dental and/or orthodontic use in a mouth of a patient. The appliance 10 may be worn by a patient of approximately three years to eight years of age. However, patients of other ages may also use the appliance 10. The appliance 10 may be constructed from rubber, plastic, silicone and/or like material. The appliance 10 may be constructed from a resilient material. The resiliency of the appliance 10 may improve the comfort and/or performance of the device for the patient when worn in the mouth.

In an embodiment, the appliance 10 may have an upper body 12 and a lower body 14. The upper body 12 and/or the lower body 14 may be generally U-shaped to correspond to the oral anatomy of the patient and/or fit within the mouth of the patient. Of course, the shape of the upper body 12 and/or the lower body 14 may be configured in a variety of shapes to fit variations in oral anatomy of patients. The variations in oral anatomy of patients may be due to mouth size, mouth shape, arch of the dentition of the patient, age of the patient, ethnicity of the patient and the like. Thus, the general U-shape of the upper body 12 and/or the lower body 14 may be narrowed, broadened, lengthened and/or shortened depending on the patient. The shape of the upper body 12 and/or the lower body 14 may be designed for the anatomy of any patient.

The upper body 12 may have an anterior portion 16 and a posterior portion 18 located opposite the anterior portion 16. The anterior portion 16 may be positioned near and/or at a front of the oral cavity of the patient when the appliance 10 is worn by the patient. The posterior portion 18 may be positioned furthest within the oral cavity of the patient when the appliance 10 is worn by the patient. Thus, the anterior portion 16 of the upper body 12 may be located adjacent to the labial area behind the lips in the front of the mouth of the patient. The upper body 12 may be located adjacent to the upper teeth in the upper jaw, maxilla and palate of the patient when the appliance 10 may be worn in the mouth of the patient.

The lower body 14 may also have an anterior portion 20 and a posterior portion 22 located opposite the anterior portion 20. The anterior portion 20 may be positioned near and/or at a front of the oral cavity of the patient when the appliance 10 may be worn by the patient. The posterior portion 22 may be positioned furthest within the oral cavity of the patient when the appliance 10 is worn by the patient. Thus, the anterior portion 20 of the lower body 14 may be located adjacent to the labial area behind the lips in the front of the mouth of the patient. The lower body 14 may be located adjacent to the lower teeth in the lower jaw and/or mandible of the patient when the appliance is worn in the mouth of the patient.

The posterior portion 18 of the upper body 12 may have posterior ends 24. The posterior ends 24 of the posterior portion 18 of the upper body 12 may be positioned furthest with the oral cavity and/or near a rear of the oral cavity of the patient when the appliance 10 is worn by the patient. Thus, the posterior ends 24 of the upper body 12 may be located near the back of the mouth near the upper molars of the patient.

The posterior portion 22 of the lower body 14 may also have posterior ends 26. The posterior ends 26 of the posterior portion 22 of the lower body 14 may be positioned furthest with the oral cavity and/or near a rear of the oral cavity of the patient when the appliance 10 is worn by the patient. Thus, the posterior ends 26 of the lower body 14 may be located near the back of the mouth near the lower molars of the patient.

In an embodiment of the invention, the appliance 10 may be designed to advance the maxilla by the patient pressing the tongue against the anterior portion of the maxilla which may advance the upper jaw forward. In an embodiment, the upper body 12 of the appliance 10 may have an upper base 30, and the lower body 14 may have a lower base 31. The upper base 30 may receive the upper teeth of the patient and the lower base 31 may receive the lower teeth of the patient. The lower base 31 may also have a lower labial shield 32. However, no labial shield may be provided on the upper base 30.

Depending on the shape and/or size of the appliance 10 with respect to the oral cavity and the upper dentition of the patient, some of the upper teeth may not contact and/or fit within and/or on the upper base 30. Also, the upper base 30 may have an elevated portion 35. The elevated portion 35 may be located near the posterior portion 18 of the upper body 12 of the appliance 10. The elevated portion 35 may extend from the posterior ends 24 in an anterior direction toward the anterior portion 16 of the upper body 12. The upper body 12 may also have upper walls 37 attached to the upper body 12. The upper walls 37 may extend vertically upward from an outer periphery of the posterior portion 18 of each of an upper left side surface 38 and an upper right side surface 39 on the upper base 30 of the upper body 12. The upper base 30 may receive some and/or all of the upper dentition. The upper posterior teeth, for example, molars, may fit on the upper base 30 within the upper walls 37. When the patient may wear the appliance 10, the elevated portion 35 may depress the upper posterior teeth. The depression of the upper posterior dentition may deepen the bite of the patient by also encouraging the upper front teeth to erupt.

Also, the upper walls 37 may also provide an increased level of safety for the patient. For example, the upper walls 37 may increase the physical size of the appliance 10 so that the upper walls 37 may inhibit excessive and/or unwanted movement of the appliance 10 within the mouth of the patient. Also, the upper walls 37 may inhibit the appliance 10 from being swallowed.

To augment the advancement of the maxilla, an embodiment of the appliance 10 may also have protrusions and/or tabs extending in an upward and/or rearward orientation in three areas, for example. In an embodiment, a central tab 40 may be provided by and above the upper central incisors of the patient. In addition, side tabs 41 may also be provided on each side of the central tab 40. The side tabs 41 may be lingual to and/or above the upper laterals and/or canines on each side of the interior of the mouth of the patient. Thus, three tabs 40, 41 may be provided in an embodiment. However, the invention is not limited to a certain number of tabs and other numbers of tabs may be provided within the scope of this present invention.

The central tab 40 may have a front surface 42 and a rear surface 43. The front surface 42 of the central tab 40 may be generally planar. Similarly, the side tabs 41 may have a front surface 44 and/or a rear surface 45. The front surface 44 of the side tabs 41 may also be generally planar.

When the appliance 10 may be worn by the patient, the front surface 42 of the central tab 40 and/or the front surface 44 of one and/or both of the side tabs 41 may contact the maxilla. The combination of the front surface 42 of the central tab 40 and the front surface 44 of one and/or both of the side tabs 41 on the upper portion of the body 15 may push across the whole segment of the maxilla. Thus, the combination of the front surface 42 of the central tab 40 and/or the front surface 44 of one and/or both of the side tabs 41 may create more complete pressure across the whole area of the pre-maxillary region.

Figure 4:
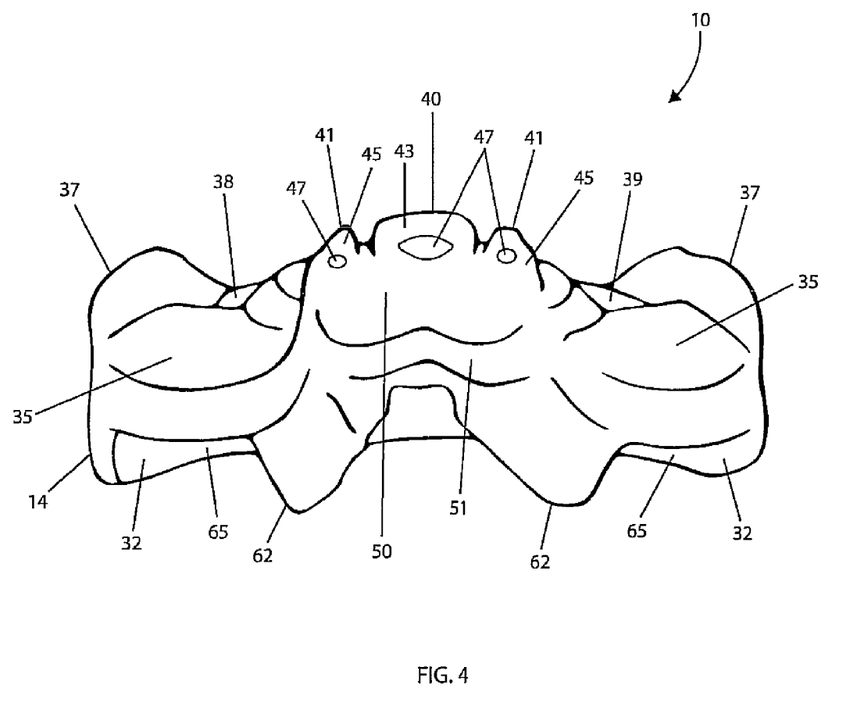
FIG. 4 illustrates a rear view of an oral appliance in an embodiment of the present invention.

In an embodiment shown in FIG. 4, reminder bumps 47 may be located at an upper margin on the rear surface 43 of the central tab 40 and/or at an upper margin on the rear surface 45 of one and/or both of the side tabs 41. The reminder bumps 47 may be integrally formed on the rear surface 43 of the central tab 40 and/or at an upper margin on the rear surface 45 of one and/or both of the side tabs 41. The reminder bumps 47 may be a raised protrusion detectable by the tongue of the patient. The reminder bumps 47 may have a generally round, oval, oblong and/or triangular shape. However, any shape may be used. Thus, the reminder bumps 47 may be used as a guide for the patient when the appliance 10 may be worn by the patient.

For example, the tongue of the patient may feel for the reminder bumps 47 on the rear surface 43 of the central tab 40 and/or one and/or both of the reminder bumps 47 on one and/or both of the rear surface 45 of the side tabs 41. The reminder bumps 47 may provide a convenient indication for the patient of a proper region of the appliance 10 on which to exert pressure.

Further, the appliance 10 may have an upper anterior lingual section 50 located near the central tab 40 and/or the side tabs 41. The tongue of the patient may push against the reminder bumps 47 on the rear surface 43 of the central tab 40 and/or the rear surface 45 of one and/or both of the side tabs 41. The pressure that may be generated by the tongue of the patient against the rear surface 43 of the central tab 40 and/or the rear surface 45 of one and/or both of the side tabs 41 may cause the front surface 42 of the central tab 40 and/or the front surface 44 of one and/or both of the side tabs 41 to contact the anterior portion of the palate of the patient. Thus, the pressure exerted by the tongue of the patient may translate forward against the anterior portion of the palate to push the palate forward. The pressure generated from this activity may advance the entire maxilla in the proper area. Further, the tongue pushing against the maxilla may open the transverse palatal suture to allow the whole maxilla to be pushed in an anterior and/or forward position. The pushing of the tongue in this manner may assist with correcting the Class III mandibular overgrowth in patients of a young age, in particular.

In an embodiment, the upper anterior lingual section 50 of the appliance 10 may have a shelf 51. The shelf 51 may be located below the rear surface 43 of the central tab 40 and/or the rear surface 45 of one and/or both of the side tabs 41. The shelf 51 may slant forward and upward to guide the tongue upward to the highest position for accurate positioning of the appliance 10 against the anterior palate and the maxilla of the patient. Thus, in addition to the reminder bumps 47 on the rear surface 43 of the central tab 40 and/or one and/or both of the reminder bumps 47 on one and/or both of the rear surface 45 of the side tabs 41, the gradual incline on the shelf 51 of the upper lingual section 50 may also be used to guide the tongue to advance the entire maxilla in the proper direction.

Further, a ramp 52 may extend at an angle relative to the upper base 30 on the anterior portion 20 of the upper body 12. The ramp 52 may exert a force on the upper incisors and may guide the upper incisors forward and downward when the appliance 10 is worn within the mouth of the patient. The angle of the ramp 52 may guide the upper incisors forward and/or downward to increase overjet and/or overbite of the patient. Doing so may also assist with correcting the Class III mandibular overgrowth in patients of a young age.

In addition to the anterior and/or forward pressure exerted by the tongue against the upper lingual section 50, and in particular, the reminder bumps 47 on the rear surface 43 of the central tab 40 and/or one and/or both of the reminder bumps 47 on one and/or both of the rear surface 45 of the side tabs 41, pressure may be exerted concurrently against the lower dentition in a posterior and/or rearward direction. The concurrent rearward pressure may be the result of a bumper 55. The bumper 55 may be a labially enlarged area across the labial portion of the lower labial shield 32 on the anterior portion 20 of the lower portion 14 of the appliance 10. The rearward pressure against the lower dentition may also assist with correcting the Class III mandibular overgrowth in patients of a young age. The lips of the patient may exert pressure against the bumper 55 to urge the lower dentition in a posterior direction. The lips and labial structure of the mouth may provide a continuous force against the bumper 55 while the appliance 10 may be worn in the mouth of the patient.

Figure 5:
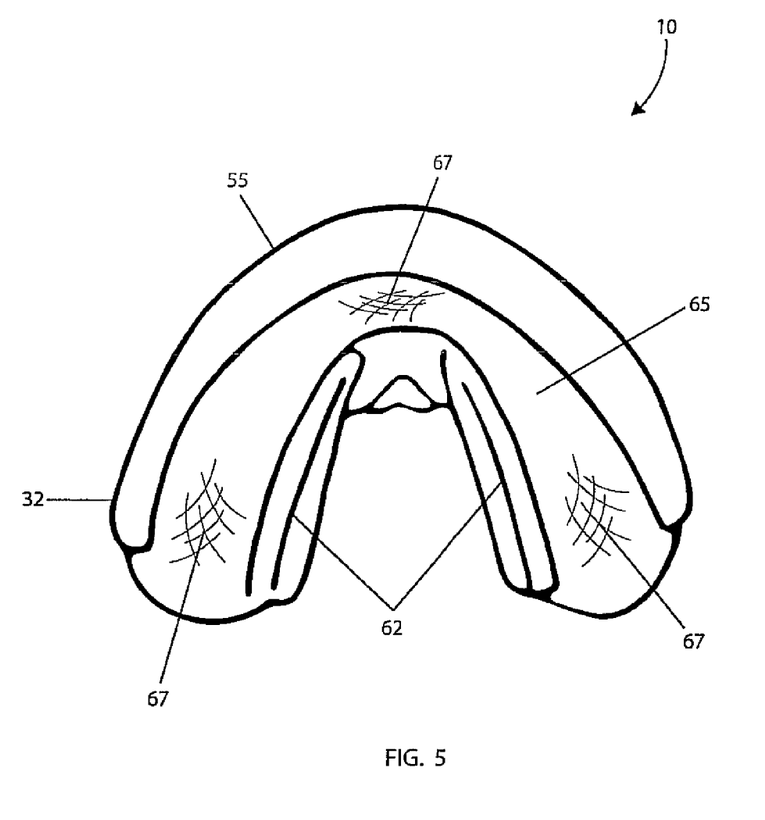
FIG. 5 illustrates a bottom view of an oral appliance in an embodiment of the present invention.

Referring now to FIGS. 4 and 5, in an embodiment, the lower body 14 of the appliance 10 may have the lower labial shield 32 arranged at an outer periphery of the lower body 14. The lower body 14 may also have inner ridges 62. The lower labial shield 32 and the inner ridges 62 may define a lower trough 65. The lower trough 65 may receive some and/or all of the lower dentition of the patient when the appliance 10 may be worn in the mouth of the patient. Depending on the shape and/or size of the appliance 10 with respect to the oral cavity and the lower dentition of the patient, some of the lower teeth may not fit within the lower trough 65.

As shown in the figures, the lower body 14 may be combined with the upper body 12 to form the appliance 10. The lower trough 65 formed in the lower base 31 of the appliance 10 may be defined by the lower labial shield 32 on the outer periphery of the lower body 14 and by the inner ridges 62 at the inner periphery of the lower body 14.

Figure 6:
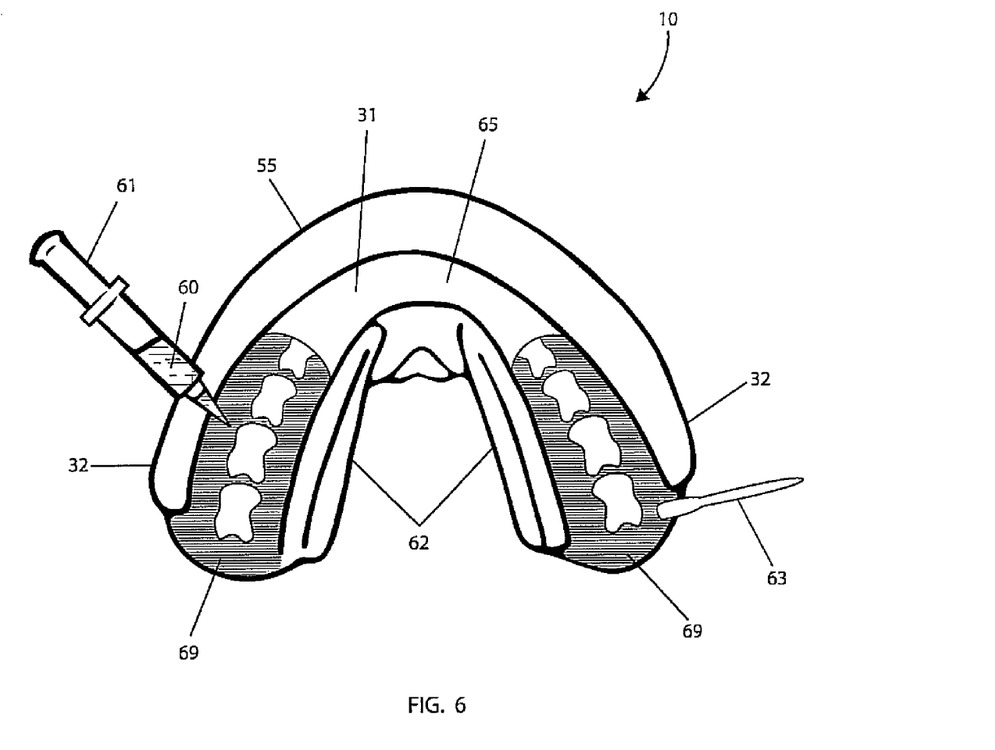
FIG. 6 illustrates a bottom view of an oral appliance in an embodiment of the present invention.

In an embodiment, a method may be provided which may increase retention of the appliance 10 in the mouth of the patient and/or the effectiveness of the correction of the malocclusion using the appliance 10. For example, the lower trough 65 on the lower base 31 of the lower body 14 may receive a reline material 60, as illustrated in FIG. 6. The reline material 60 may be a self-cure acrylic, for example. In an embodiment, the reline material 60 may be injected from, for example, a syringe 61. The reline material 60 may also be applied, for example, using a spatula 63 to spread the reline material 60 on the lower trough 65, as desired.

In an embodiment, the lower base 31 of the lower body 14 of the appliance 10 may have textured, coarse and/or roughened surfaces 67, hereinafter, surfaces 67. The surfaces 67 may be located on the lower trough 65 within and/or along the lower labial shield 32 and/or the inner ridges 62. The surfaces 67 may secure the reline material 60. The surfaces 67 may prevent the reline material 60 from becoming disengaged from the lower base 31. The surfaces 67 may provide for better adherence of the reline material 60 to the lower trough 65 of the appliance 10. After inserting the reline material 60 onto the surfaces 67 of the lower trough 65, the appliance 10 may be placed in the mouth of the patient. The appliance 10 may be pressed forcibly against the lower teeth of the patient. In particular, the lower base 31 may be forcibly pushed down on the lower teeth. The patient may also then bite down to maintain the appliance 10 under pressure until the reline material 60 has set. When the reline material 60 may be set, the appliance 10 may be removed from the mouth of the patient.

In an embodiment, the reline material 60 may be allowed to harden in the mouth of the patient for 2½ minutes, for example. The reline material 60 may flow around and at least partially surround and/or encapsulate the lower dentition to form a lining 69 of hardened reline material 60. The lining 69 of hardened reline material 60 may be form-fitting lining on at least some of the posterior lower teeth as shown in FIG. 6. The lining 69 may provide a more secure and/or snug fit between the appliance 10 and the lower dentition of the patient. Thus, the reline material 60 may secure the appliance 10 to the teeth of the patient when hardened into the lining 69. A purpose of the lining 69 may be to allow the whole lower dentition of the patient to be moved in a distal and/or rearward direction when the appliance 10 may be worn in the mouth of the patient.

The reline material 60 may be placed on the appliance 10 in any areas in which teeth may be contacted. For example, in certain cases where indicated, the lower front teeth, for example, incisors, in the front of the lower trough 65 may also be lined with the reline material 60. Thus, the lower front teeth may be permitted to be moved without being tipped when being moved in a rearward direction. In other cases, however, the lower front teeth in the front of the lower trough 65 may not be lined with the reline material 60. For example, in cases of crowding of the lower front teeth, it may be preferred to not line the lower front teeth in the front of the lower trough 65 with the reline material 60. Thus, the posterior lower teeth may be distalized and/or moved in a rearward direction which may provide more room for the front lower teeth to move which may alleviate the crowding of the lower front teeth.

Figure 1:
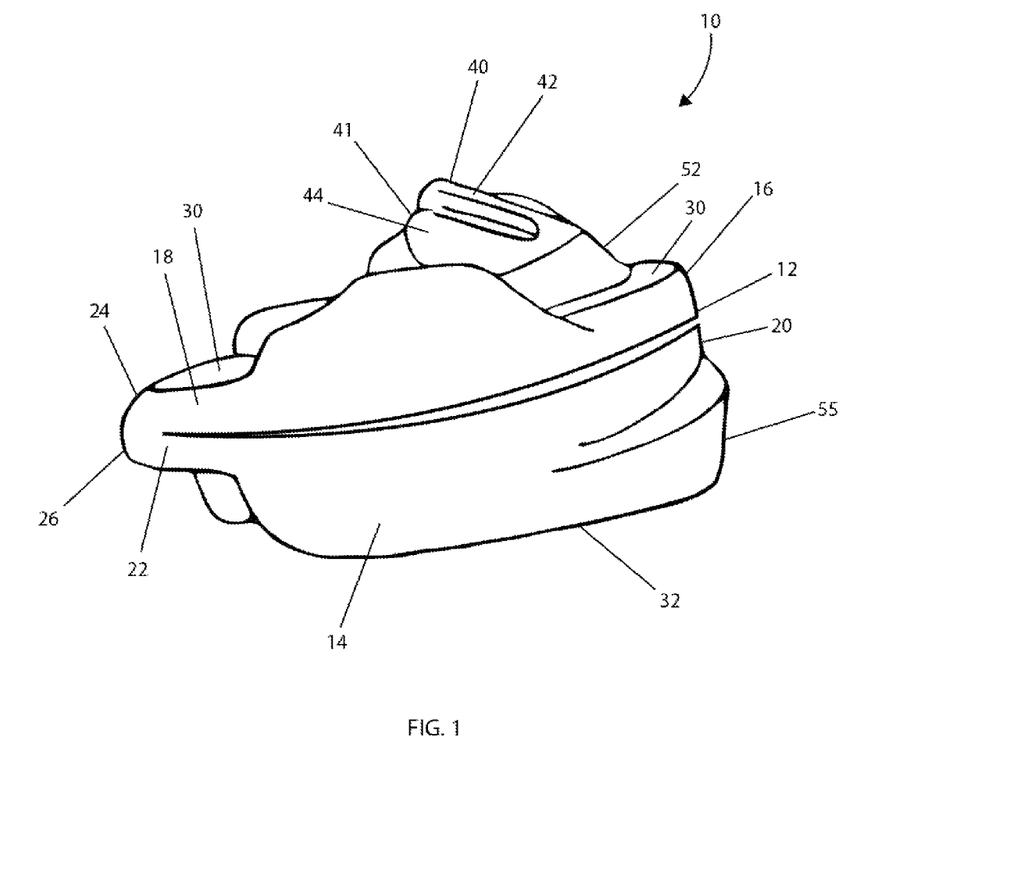
FIG. 1 illustrates a side view of an oral appliance in an embodiment of the present invention.
Figure 2:
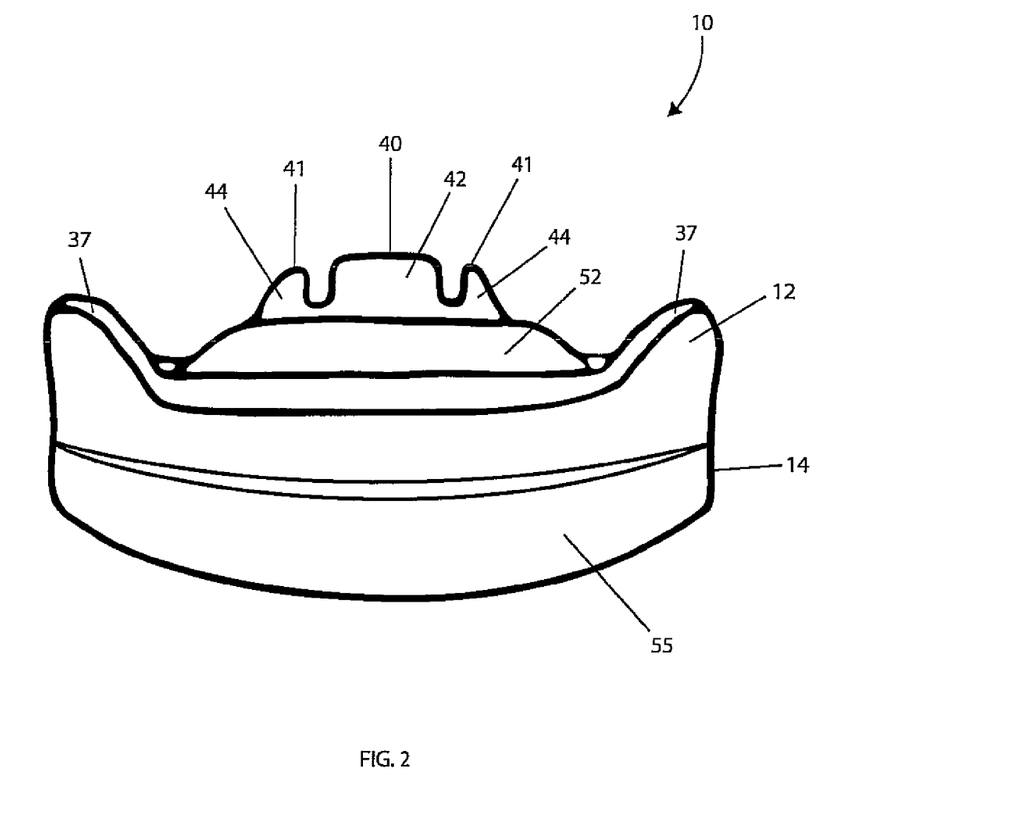
FIG. 2 illustrates a front view of an oral appliance in an embodiment of the present invention.
Figure 3:
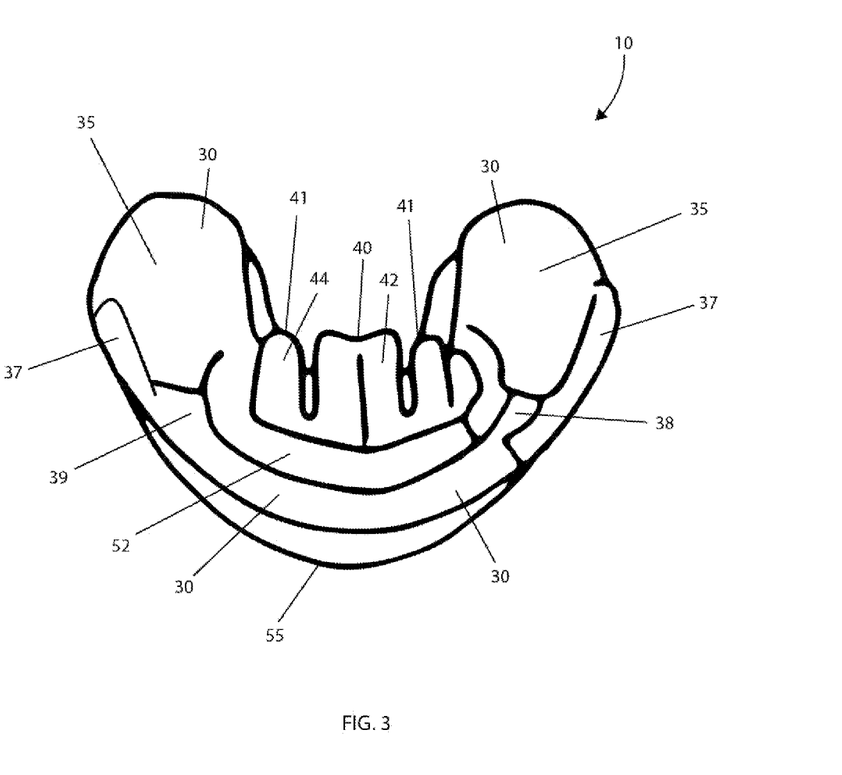
FIG. 3 illustrates a top view of an oral appliance in an embodiment of the present invention.

In an embodiment, the appliance 10 may be hinged as shown in FIG. 1. The lower body 14 may be joined with the upper body 12 near the posterior ends 26 to allow the opening of the upper jaw and/or the lower jaw of the patient. The hinged appliance 10 may provide an increased level of comfort to the patient. In particular, when a young child may wear the appliance 10 in the mouth, the appliance 10 may be stabilized in the mouth of the patient. The hinged construction of the appliance 10 may also provide an increased level of safety to the patient. For example, the hinged construction of the appliance 10 may inhibit excessive and/or unwanted movement of the appliance 10 within the mouth of the patient and/or may inhibit aspiration of the appliance 10.

Accordingly, the appliance 10 may be worn by the patient at night while the patient is lounging, resting and/or sleeping, for example. However, use of the appliance 10 during waking hours may enhance the correction and/or shorten the time required for correction of the malocclusion. Preferably, the patient may wear the appliance 10 while sleeping and two hours during the day when pushing the tongue against the upper anterior portion of the palate.

The patient may perform exercises which may correct malocclusions while requiring a lesser amount of cooperation than required with known appliances. To this end, the patient may press the tongue forward against the reminder bumps 47 on the rear surface 43 of the central tab 40 and/or one and/or both of the reminder bumps 47 on one and/or both of the rear surface 45 of the side tabs 41. Further, movement of the teeth may reduce an amount of exercise or other cooperation required for correction of the malocclusion. If space is required within the mouth of the patient due to crowding of teeth, one or more teeth may be stripped and/or removed prior to wearing of the appliance 10.

As a result, the patient may reduce a need for wearing the appliance during, for example, the daytime when the patient is awake or active. However, an overall time period during which a malocclusion is corrected may be extended. In an example, the overall time period for the patient to correct the malocclusion may be extended from a period of four months to ten months to a period of two years or more with reduced wearing of the appliance during the time the patient is awake or active.

Figure 7:
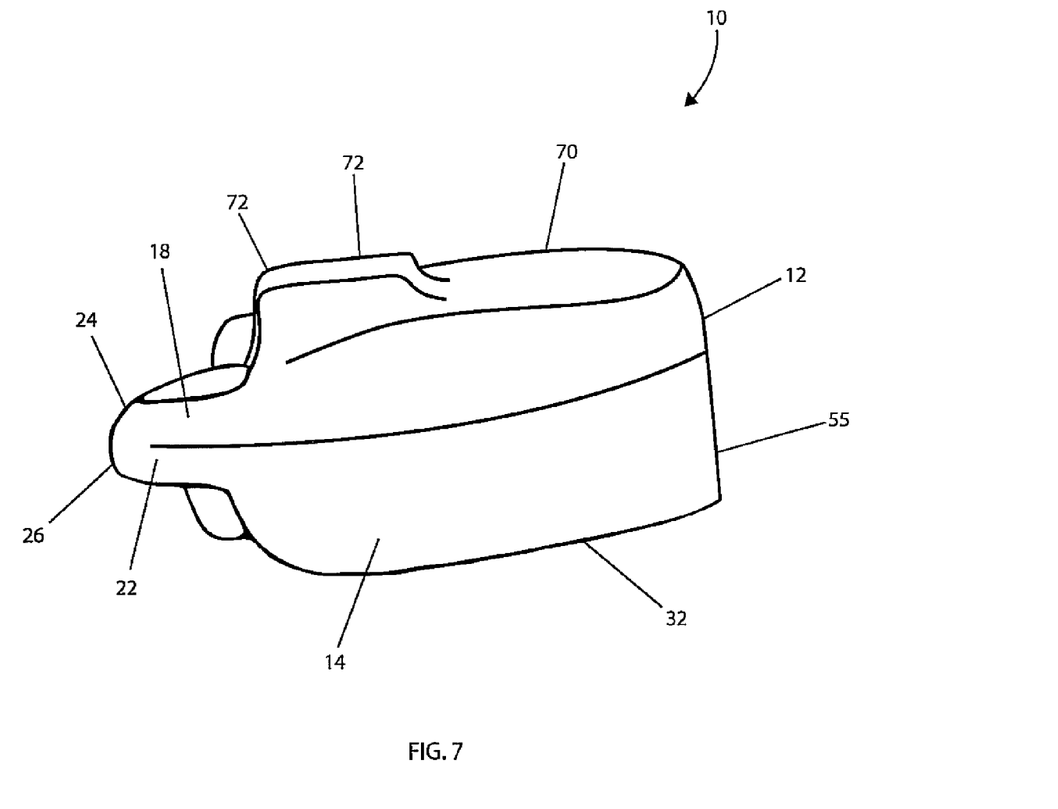
FIG. 7 illustrates a side view of an oral appliance in an embodiment of the present invention.
Figure 8:
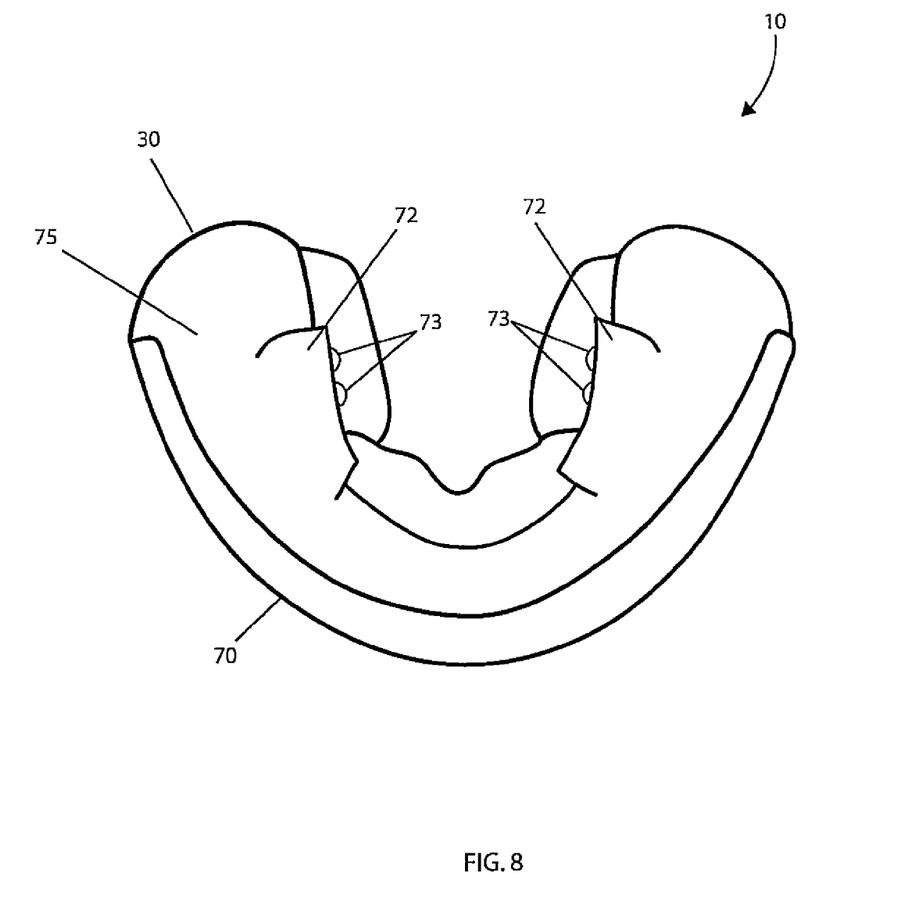
FIG. 8 illustrates a top view of an oral appliance in an embodiment of the present invention.

In another embodiment illustrated in FIGS. 7 and 8, the upper body 12 of the appliance 10 may have an upper labial shield 70 arranged at an outer periphery of the upper body 12. The upper body may also have lateral palatal tabs 72 arranged at an inner periphery of the posterior portion 18 of the upper body 12. The upper labial shield 70 and the palatal tabs 72 may define an upper trough 75. The upper trough 75 may receive some and/or all of the upper dentition of the patient when the appliance 10 may be worn in the mouth of the patient. Depending on the shape and/or size of the appliance 10 with respect to the oral cavity and the upper dentition of the patient, some of the upper teeth may not fit within the upper trough 75.

As shown in FIGS. 7 and 8, the palatal tabs 72 may be formed on and/or may be attached at the inner periphery of the upper body 12 of the appliance 10. The palatal tabs 72 may be integrally formed with the appliance 10. The palatal tabs 72 of the appliance 10 may be adjacent to, may contact and/or may abut the palate of the patient.

The palatal tabs 72 may provide a surface against which the patient may exert pressure. For example, the patient may be instructed to elevate the palate by pushing the tongue against the palatal tabs 72. The tongue pressing against the palatal tabs 72 may exert lateral pressure that may widen a narrowed palate that may be caused, for example, by thumb sucking and/or finger sucking. The tongue pressing against the palatal tabs 72 may also inhibit and/or prevent narrowing of the palate with a continuing habit of thumb sucking. Further, the tongue pressing against the palatal tabs 72 may exert lateral pressure that may widen a narrowed palate in an instance in which advancement of the maxilla in a forward direction may not desired and/or indicated for the condition of the patient.

As shown, in an embodiment, the palatal tabs 72 may also have circular bumps 73 to remind the tongue where to push. The bumps 73 may be circular and/or spherical. It should be understood that the bumps 73 may be constructed in any shape as known by one having ordinary skill in the art.

Further, the bumps 73 on the palatal tabs 72 may remind the patient to move the tongue of the patient to the correct position during closure of the oral cavity and/or during wear of the appliance 10 in the closed position. Moreover, the palatal tabs 72 may encourage the patient to move the tongue of the patient to the correct position during the swallowing movements by the patient and/or during the resting periods between the swallowing movements by the patient.

Moreover, the present invention is not limited to the specific arrangement of the components illustrated in the figures. It should be understood that various changes and modifications to the presently preferred embodiments described herein will be apparent to those having ordinary skill in the art. Such changes and modifications may be made without departing from the spirit and scope of the present invention and without diminishing its attendant advantages. It is, therefore, intended that such changes and modifications be covered by the appended claims.

I claim:

1. An appliance for correcting a malocclusion in a mouth of a user, the appliance comprising:
    a generally U-shaped upper body having an anterior portion configured to be adjacent to upper incisors and a posterior portion located rearward to the anterior portion, the upper body having an upper base with a perimeter defining an outer boundary and walls extending along the perimeter of the posterior portion of the upper body;
    a generally U-shaped lower body having an anterior portion configured to be adjacent to lower incisors, the lower body having a lower base with a perimeter defining an outer boundary, the lower base having a width which is configured to be greater than a width of the teeth of the user and wherein the lower body has walls extending along the perimeter of the lower body to define a trough, the trough being configured to contact the lower incisors as the appliance is worn in the mouth of the user;
    lingual protrusions extending rearward from the anterior portion of the upper body, the lingual protrusions being configured to contact a maxilla when the appliance is worn within the mouth of the user; and
    a bumper that is configured to define a labially enlarged area with respect to the outer boundary across a labial portion of the anterior portion of the lower body of the appliance so that a rearward force is configured to be exerted by the lips of the user against the bumper and cause a lower jaw of the user to move rearward relative to an upper jaw of the user as the lower appliance is worn within the mouth of the user.

2. The appliance of claim 1 further comprising:
    a raised surface on the posterior portion of the upper base of the upper body.

3. The appliance of claim 1 further comprising:
    a shelf that projects generally horizontally from the upper body, the shelf being adjacent to the upper anterior base and being configured to extend rearward in the mouth of the user to provide a surface that is configured to guide a tongue as the appliance is worn within the mouth of the user.

4. The appliance of claim 1 further comprising:
    a ramp that extends at an angle relative to the upper base on the anterior portion of the upper body, the ramp being configured to exert a force on the upper incisors and guide the upper incisors forward and downward as the appliance is worn within the mouth of the user.

5. The appliance of claim 1 wherein the upper base is configured to contact the furthest forward upper teeth within the mouth.

6. The appliance of claim 1 further comprising:
a raised protrusion on one of the lingual protrusions, the raised protrusion being configured to direct a tongue as the appliance is worn within the mouth of the user.

7. The appliance of claim 1 further comprising:
a reline material in contact with the trough in the lower body, the reline material being configured to adhere the lower body to lower teeth and to exert a force against the lower teeth to thereby cause the lower teeth to move rearward as the appliance is worn in the mouth of the user.

8. The appliance of claim 1 wherein the appliance is constructed from a resilient material.

9. The appliance of claim 1 wherein the trough has a roughened surface.

10. The appliance of claim 1 wherein the lingual protrusions have a center tab extending rearward from a center of the anterior portion of the upper body and a side tab adjacent to each side of the center tab and extending rearward from the anterior portion of the upper body, the center and side tabs being configured to move the maxilla and upper teeth forward with respect to the mouth in response to pressure from a tongue.

11. The appliance of claim 10 wherein the side tabs are configured to encourage the tongue to exert pressure against the palatal tabs to encourage a widening of the palate.

12. The appliance of claim 1 further comprising palatal tabs on the posterior portion of the upper body, the palatal tabs being configured to receive pressure exerted by a tongue to encourage a widening of the palate.

13. An orthodontic system worn adjacent to upper teeth and lower teeth in a mouth of a user, the orthodontic system comprising:
an upper appliance having an anterior portion and a posterior portion located rearward of the anterior portion, the posterior portion being shaped to contact upper molars, and wherein the upper appliance has an inner perimeter and an outer perimeter, the outer perimeter being located exterior to the inner perimeter;
a lower appliance having an outer shield, the outer shield extending vertically downward from the lower appliance to define a trough in the lower appliance, and wherein the lower appliance is shaped to contact lower incisors and lower molars;
a lining configured to contact lower teeth in the trough, the lining being configured to adhere the lower appliance to the lower teeth and to exert a force against the lower teeth and a lower jaw, the exerted force being configured to move the lower jaw rearward with respect to an upper jaw as the upper appliance and the lower appliance are worn in the mouth of the user;
a ramp configured to extend around the inner perimeter and contact upper incisors to move the upper incisors forward and downward, the ramp having a first anterior end and a first posterior end located rearward with respect to the first anterior end, and wherein the ramp extends rearward and diagonally from the inner perimeter of the upper appliance such that the first posterior end is positioned higher than the first anterior end;
a tab having a second anterior end and a second posterior end located rearward with respect to the second anterior end, the tab extending rearward and diagonally from the first posterior end of, and to a position higher than, the ramp such that the second posterior end is positioned higher than the second anterior end, and wherein the tab is configured to contact the upper jaw of the user and apply a force to move the upper jaw forward relative to the lower jaw as the appliance is worn within the mouth of the user;
a bumper that is configured to receive an exerted rearward force from the lips of the user to cause the lower jaw to move rearward relative to the upper jaw as the lower appliance is worn within the mouth of the user; and
a hinge that connects the upper appliance to the lower appliance.

14. The system of claim 13 further comprising:
an elevated surface on the posterior portion of the upper appliance, the elevated surface being shaped to depress the upper molars as the upper appliance is worn within the mouth of the user.

15. The system of claim 13 further comprising:
a shelf in the upper appliance, the shelf forming a cavity with the tab behind the anterior portion of the upper appliance.

16. An appliance for correcting a malocclusion in a mouth of a user, the appliance comprising:
a generally U-shaped upper body having an anterior portion configured to be adjacent to upper incisors and a posterior portion located rearward to the anterior portion, the upper body having an outer perimeter and an inner perimeter that is located interior to the outer perimeter;
a generally U-shaped lower body having an outer perimeter, the outer perimeter of the lower body having an anterior portion adjacent to lower incisors and a posterior portion located rearward to the anterior portion of the lower body, wherein the lower body has a lower labial shield extending along the outer perimeter of the lower body, the lower labial shield having a bumper that is configured to define a labially enlarged area with respect to the outer perimeter across a labial portion of the anterior portion of the lower body of the appliance so that lips of the user are configured to exert a rearward force against the bumper and move a lower jaw of the user rearward relative to an upper jaw of the user as the lower appliance is worn within the mouth of the user; and
lingual protrusions extending generally upward from the posterior portion of the inner perimeter of the upper body, the lingual protrusions being configured to contact a palate of the user as the appliance is worn within the mouth of the user.

* * * * *